US 11,744,702 B1

(12) United States Patent
Shahriari et al.

(10) Patent No.: US 11,744,702 B1
(45) Date of Patent: Sep. 5, 2023

(54) TRANSCATHETER AORTIC VALVE REPAIR AND REPLACEMENT

(71) Applicant: Aortic Innovations, LLC, Hillsboro Beach, FL (US)

(72) Inventors: Ali Shahriari, Boca Raton, FL (US); Justin Nifong, Lexington, NC (US)

(73) Assignee: Aortic Innovations, LLC, Hillsboro Beach, FL (US)

( * ) Notice: Subject to any disclaimer, the term of this patent is extended or adjusted under 35 U.S.C. 154(b) by 112 days.

(21) Appl. No.: 17/365,975

(22) Filed: Jul. 1, 2021

Related U.S. Application Data (60) Provisional application No. 63/046,709, filed on Jul. 1, 2020.

(51) Int. Cl.
  *A61F 2/24* (2006.01)
  *A61L 31/04* (2006.01)
  *A61F 2/07* (2013.01)
  *A61L 27/14* (2006.01)

(52) U.S. Cl.
  CPC .............. *A61F 2/2418* (2013.01); *A61F 2/07* (2013.01); *A61F 2/24* (2013.01); *A61L 27/14* (2013.01); *A61L 31/041* (2013.01); *A61F 2220/0075* (2013.01); *A61F 2250/0069* (2013.01); *A61L 2430/20* (2013.01)

(58) Field of Classification Search
  CPC .. A61F 2/24; A61F 2/2418; A61F 2/07; A61F 2/848; A61F 2002/075; A61F 2220/0075; A61F 2002/8486; A61F 2002/821; A61F 2002/067; A61F 2002/061; A61F 2240/001; A61F 2/90; A61F 2/82; A61F 2/06; A61F 2/246; A61F 2/856; A61F 2/86; A61F 2002/065; A61F 2/0077; A61F 2/962; A61F 2250/0069
  See application file for complete search history.

(56) References Cited

U.S. PATENT DOCUMENTS

| | | | | |
|---|---|---|---|---|
| 4,517,687 A | * | 5/1985 | Liebig | D03D 27/00 428/36.1 |
| 4,652,263 A | * | 3/1987 | Herweck | A61F 2/06 623/1.33 |
| 4,695,280 A | * | 9/1987 | Watanabe | A61L 27/16 623/1.54 |
| 4,892,539 A | * | 1/1990 | Koch | A61F 2/06 600/36 |
| 5,370,682 A | * | 12/1994 | Schmitt | D03D 3/02 600/36 |

(Continued)

*Primary Examiner* — Seema Mathew
(74) *Attorney, Agent, or Firm* — NK Patent Law (57) ABSTRACT

A heart valve assembly includes an outer frame. The outer frame is formed from a metallic material and defines a gridded configuration. An inner frame houses a prosthetic heart valve. The inner frame is a graft covering extending around the prosthetic heart valve for providing sealing to the heart valve. The graft covering is one of polyester, PTFE, ePTFE, or a polymer. The outer frame is secured to the graft covering. The outer frame is secured to the graft covering by a plurality of stitches. A plurality of radially extending fibers extend from the graft covering and through the outer metallic frame to form a seal positioned outwardly of the outer frame. The fibers include strands of fibers that terminate in an end thereof outwardly of the outer frame.

1 Claim, 9 Drawing Sheets

(56) References Cited

U.S. PATENT DOCUMENTS

| | | | | |
|---|---|---|---|---|
| 6,547,820 | B1* | 4/2003 | Staudenmeier | D04B 21/02 |
| | | | | 264/103 |
| 2002/0099441 | A1* | 7/2002 | Dehdashtian | A61F 2/07 |
| | | | | 623/1.36 |
| 2002/0151958 | A1* | 10/2002 | Chuter | A61B 17/12022 |
| | | | | 623/1.13 |
| 2003/0120332 | A1* | 6/2003 | Hartley | A61F 2/07 |
| | | | | 623/1.36 |
| 2003/0139806 | A1* | 7/2003 | Haverkost | A61L 27/48 |
| | | | | 623/1.33 |
| 2004/0044397 | A1* | 3/2004 | Stinson | A61F 2/06 |
| | | | | 623/1.15 |
| 2004/0182511 | A1* | 9/2004 | Rakos | A61F 2/06 |
| | | | | 156/287 |
| 2004/0221623 | A1* | 11/2004 | Kantsevitcha | A61L 27/507 |
| | | | | 66/170 |
| 2006/0009835 | A1* | 1/2006 | Osborne | A61F 2/06 |
| | | | | 623/1.13 |
| 2006/0058867 | A1* | 3/2006 | Thistle | A61L 27/507 |
| | | | | 623/1.53 |
| 2006/0147612 | A1* | 7/2006 | Da Rocha Loures | A61L 31/10 |
| | | | | 427/2.25 |
| 2006/0235511 | A1* | 10/2006 | Osborne | A61F 2/2418 |
| | | | | 623/2.12 |
| 2007/0196420 | A1* | 8/2007 | Dwyer | A61F 2/06 |
| | | | | 514/56 |
| 2007/0198077 | A1* | 8/2007 | Cully | A61F 2/97 |
| | | | | 623/1.13 |
| 2007/0244569 | A1* | 10/2007 | Weber | A61L 31/148 |
| | | | | 623/1.42 |
| 2010/0016872 | A1* | 1/2010 | Bayon | A61L 27/24 |
| | | | | 606/151 |
| 2012/0265289 | A1* | 10/2012 | Macatangay | D03D 15/283 |
| | | | | 623/1.15 |
| 2019/0365530 | A1* | 12/2019 | Hoang | A61F 2/0077 |

* cited by examiner

TRANSCATHETER AORTIC VALVE REPAIR AND REPLACEMENT

CROSS-REFERENCE TO RELATED APPLICATIONS

This application claims priority to U.S. Provisional Patent Application No. 63/046,709, entitled Device for Endovascular Repair of Aortic Disease, filed on Jul. 1, 2020, and incorporated by reference herein.

TECHNICAL FIELD

The present disclosure relates to a device and method of using same for endovascular aortic valve repair or replacement. The device can be used for other valves of the heart as well. The device is configured for addressing paravalvular leakage between the valve and the native valve of the patient.

BACKGROUND

Endovascularly implanted heart valves continue to increase in market share due to their simplicity and minimally invasive nature. Compared to a surgical valve which requires entry into the chest cavity of the patient, an endovscularly implanted valve can be implanted quickly and with a much shorter recovery time period.

The endovascular deployment involves accessing an access artery, such as the femoral artery, and advancing the small valve through the artery and into place. Once in place, the valve is expanded against the native and diseased heart valve area and annulus of the patient.

Sealing of the valve against the annulus is incredibly important to prevent paravalvular leaks that can impact valve performance, or require surgical reintervention. However, maintaining a low profile to the valve is also important so that the valve can be deployed in a variety of anatomical dimensions and sufficient size can be provided for the valve leaflets.

Various attempts have been made to address paravalvular leakage. These include addition of an outer skirt outside of the frame, however, this increases valve profile and also restricts shortening and elongation of the frame assembly. Further attempts have included outer umbrella type features that flap in response to blood flow to otherwise seal off the blood flow in an interactive and responsive manner.

DETAILED DESCRIPTION

A heart valve assembly includes an outer frame. The outer frame is formed from a metallic material and defines a gridded configuration. An inner frame houses a prosthetic heart valve. The inner frame is a graft covering extending around the prosthetic heart valve for providing sealing to the heart valve. The graft covering is one of polyester, PTFE, ePTFE, or a polymer. The outer frame is secured to the graft covering. The outer frame is secured to the graft covering by a plurality of stitches. A plurality of radially extending fibers extend from the graft covering and through the outer metallic frame to form a seal positioned outwardly of the outer frame. The fibers include strands of fibers that terminate in an end thereof outwardly of the outer frame.

Prior Art Design

Figure 1:
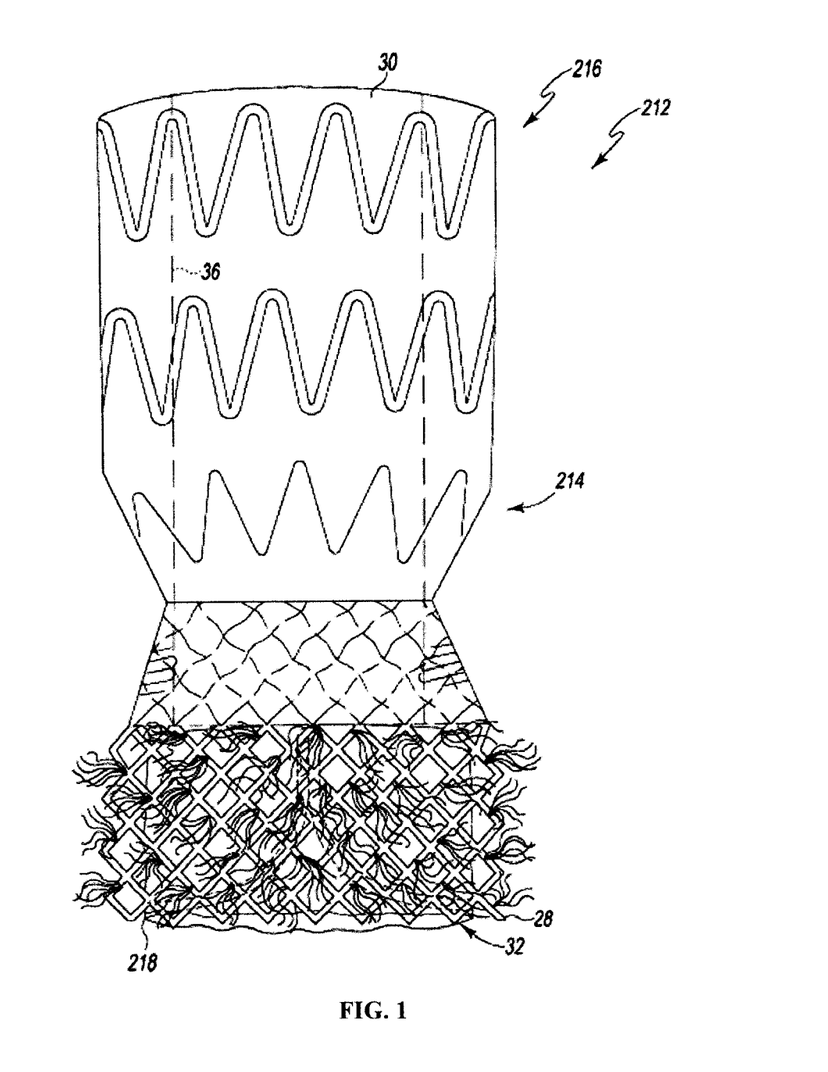
FIG. 1 illustrates a front view of a Transcatheter Valve Replacement (TVR) according to one or more embodiments disclosed herein.

A prior art heart valve is illustrated in FIG. 1.

As shown in FIG. 1, the proximal component 212 includes a dual-frame 214 that extends from a proximal end 28 to a distal end 30. The frame 214 is attached to a valve 32 (shown in phantom), which is positioned at the proximal end 28 of the component 212. In the illustrative embodiment, the valve 32 is configured as a bicuspid valve. It should be appreciated that in other embodiments the valve 32 may be tricuspid or quadracuspid. The valve 32 may be constructed from treated bovine pericardium or other suitable proven biological or synthetic material. When the proximal component 212 is implanted into the patient's aorta 16, the valve 32 replaces the aortic valve and permits fluid (i.e., blood) to selectively pass from the heart and into a passageway 36 extending through the proximal component 212.

Figure 2:
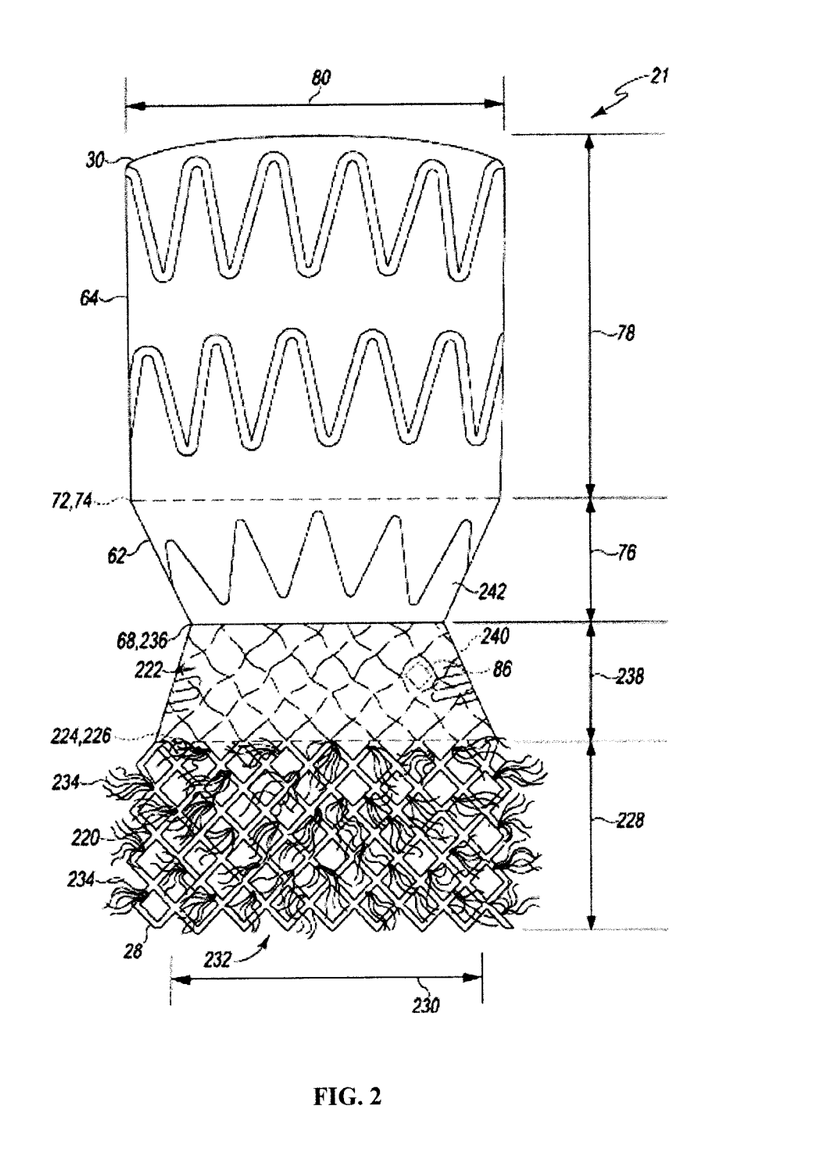
FIG. 2 illustrates another front view of the TVR of FIG. 1 according to one or more embodiments disclosed herein.

The dual-frame 214 of the proximal component 212 includes a self-expanding outer frame 216 and a balloon-expandable inner frame 218 that is secured to the self-expanding outer frame 216 and houses the valve 32. Referring now to FIG. 2, the self-expanding outer frame 216 has a generally hourglass shape and is formed from a metallic material, such as, nitinol, stainless steel, or other implant grade metallic material. It should be appreciated that in other embodiments the outer frame 216 may be formed from a polymeric material. The outer frame 216 includes an elongated proximal section 220, an inwardly tapered section 222, an outwardly tapered middle section 62, and an elongated distal section 64.

In one or more embodiments, the dual-frame design may be entirely self-expanding, or entirely balloon-expandable. Expansion of the outer frame 216 may impart expansion to the inner frame 218. A gap may be formed between the inner frame 218 and outer frame 216 in a contracted or partially expanded state, which is then closed upon expansion of the transcatheter valve assembly.

The elongated proximal section 220 of the outer frame 216 includes the proximal end 28 of the component 212 and has a distal end 224 connected to a proximal end 226 of the inwardly tapered section 222. The proximal section 220 is embodied as a tubular stent. It should be appreciated that in other embodiments the section 220 may be shaped as a prism, cone, or other geometric shape depending on the patient's anatomy.

Figure 9:
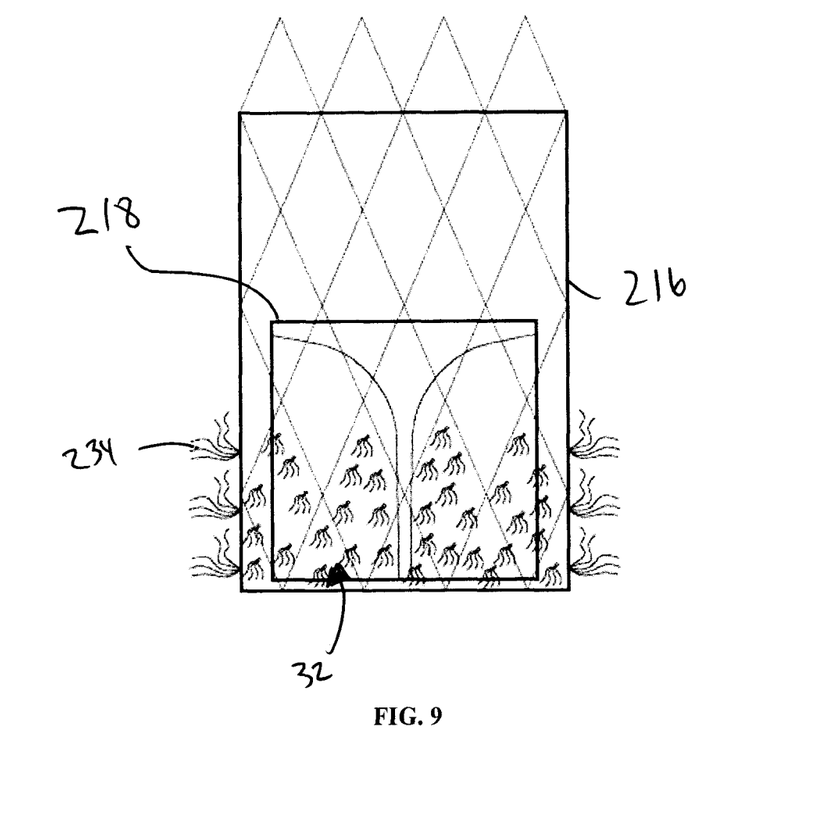
FIG. 9 illustrates a side, cross-section view of a TVR according to one or more embodiments disclosed herein.

In the illustrative embodiment, the proximal section 220 has a length 228 that is equal to approximately 15 mm. The proximal section 220 also has a diameter 230 of approximately 32 mm. It should be appreciated that in other embodiments the dimensions of the frame 216 may vary according to the anatomy of the patient. In the illustrative embodiment, the diameter 230 is oversized relative to the diameter of the aortic annulus 210 such that an interference fit is created between the proximal section 220 and the annulus 210 when the component 212 is implanted, as described in greater detail below. As shown in FIG. 9, the proximal section 220 defines a passageway 232 in the outer frame 216.

In the illustrative embodiment, collagen fibers 234 are attached to the proximal section 220 to aid in preventing paravalvular leaks and migration of the proximal component 212 within the aortic walls. The fibers 234 extend outwardly from the proximal section 220 and inwardly into the passageway 232. It should be appreciated that in other embodiments the outer frame 216 may be covered with hydrogel or other sealing materials. In other embodiments, a plurality of barbs or hooks may be attached to the proximal section 220. The hooks may be configured to further engage the tissue of the aorta and inhibit or prevent migration of the device 10.

The inwardly tapered section 222 of the outer frame 216 includes the proximal end 226 and has a distal end 236 connected to the proximal end 68 of the outwardly tapered middle section 62. The section 222 tapers inwardly between the ends 226, 236 from approximately 32 mm at the end 226 to approximately 22 mm at the end 236. In the illustrative embodiment, the inwardly tapered section 222 has a length 238 of approximately 10 mm.

The outwardly tapered middle section 62 of the self-expanding frame 216 has the proximal end 68 and a distal end 72 connected to the proximal end 74 of the elongated distal section 64. The section 62 tapers outwardly from a diameter of approximately 22 mm at the end 68 to a diameter of approximately 28 mm at the end 72. In the illustrative embodiment, the middle section 62 has a length 76 of approximately 10 mm. In other embodiments, the dimensions of the section 62 may vary depending on, for example, the patient's anatomy.

The elongated distal section 64 of the self-expanding frame 216 extends distally from the proximal end 74 to the distal end 30 of the component 212. In the illustrative embodiment, the section 64 has a length 78 that is greater than the combined length of the tapered sections 60, 62. In one particular non-limiting example, the length 78 of the elongated distal section 64 is approximately 30 mm and has a diameter 80 of approximately 34 mm. In other embodiments, the dimensions of the section 64 may vary depending on, for example, the patient's anatomy. In one exemplary embodiment, the distal section 64 may taper between the proximal end 74 and the distal end 30.

As shown in FIG. 2, the proximal section 220 and the inwardly tapered section 222 of the self-expanding frame 216 are formed in an open-cell stent configuration, and the sections 62, 64 are formed in a Z-stent configuration. It should be appreciated that in other embodiments the sections 62, 64, 220, 222 may be formed in a single configuration, including an open-cell stent configuration or Z-stent configuration. The sections 62, 64, 220, 222 may also be formed as a single monolithic component. The outer surface 240 of the sections 62, 64, 222 are covered with low profile polyester, ePTFE, or other nonporous covering material 242 such that fluid is prevented from passing through the surface 240. The covering material 242 immediately distal to the proximal section 220 is equipped with a "trap door" 86, which may be opened to permit the passage of one or more surgical instruments for embolization of possible paravalvular leaks. The outer surface 240 of the sections 62, 64, 222 may be also covered with low-profile Dacron or other synthetic material. It should also be appreciated that all or part of the frame 216 may be covered with hydrogel or other sealing material.

Figure 10:
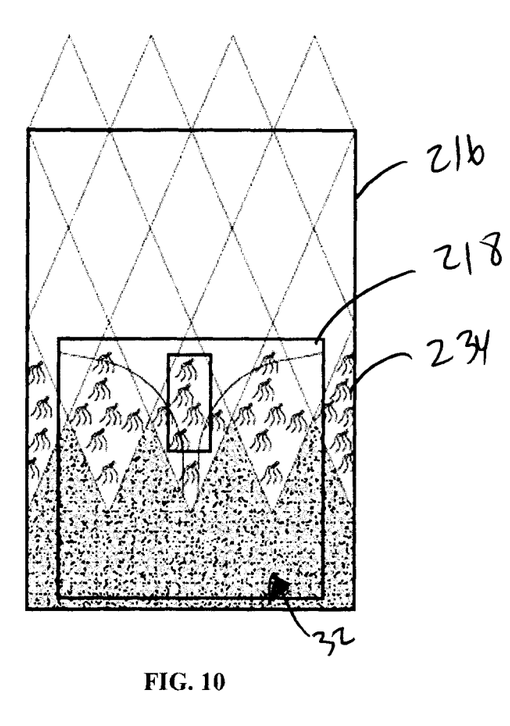
FIG. 10 illustrates a side, cross-section view of a TVR according to one or more embodiments disclosed herein.

As described above, the outer frame 216 of the dual-frame 214 is secured to a balloon-expandable inner frame 218, which is positioned in the passageway 232. As shown in FIG. 10, the frame 218 houses the valve 32. The balloon-expandable frame 218 is embodied as a balloon-expandable tubular stent 244 that has a length 246 of approximately 15 mm. In other embodiments, the stent 244 may be longer or shorter depending on, for example, the patient's anatomy. The stent 244 is tubular and is constructed of a metallic material, such as, nitinol, stainless steel, or other implant grade metallic material, in an open-cell configuration. It should be appreciated that in other embodiments the stent 244 may be formed from a polymeric material and may be formed in, for example, a Z-stent configuration. In the illustrative embodiment, the outer surface 248 of the stent 244 is covered with low-profile polyester, ePTFE, or other nonporous covering material 250 that prevents fluid from passing through the outer surface 248. However, it should be appreciated that the stent 244 may be covered with standard polyester, ePTFE or other nonporous materials.

Figure 3:
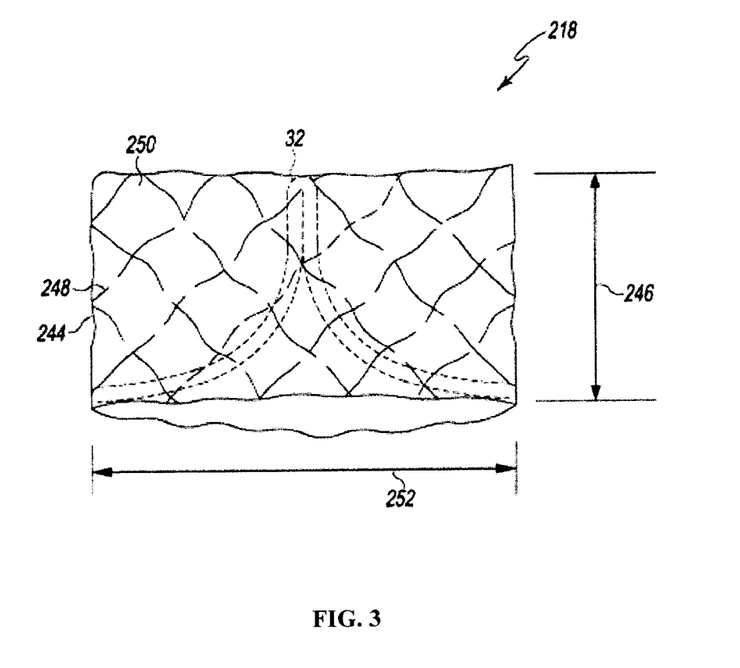
FIG. 3 illustrates a front view of an inner frame assembly carrying replacement leaflets according to one or more embodiments disclosed herein.

As shown in FIG. 3, the stent 244 of the inner frame 218 has a diameter 252. As described in greater detail below, the balloon-expandable frame 218 is expandable during implantation from an unexpanded diameter (not shown) to the expanded diameter 252. In the illustrative embodiment, the expanded diameter 252 is equal to approximately 26 mm when the inner frame 218 is expanded. In other embodiments, the expanded diameter may be equal to, or greater than, the diameter 230 of the proximal section 220 of the outer frame 216. In the illustrative embodiment, the expanded diameter 252 is oversized relative to the diameter of the aortic annulus 210 such that an interference fit is created between the proximal section 220 and the annulus 210 when the component 212 is implanted, and the inner frame 218 is expanded, as described in greater detail below.

Figure 4:
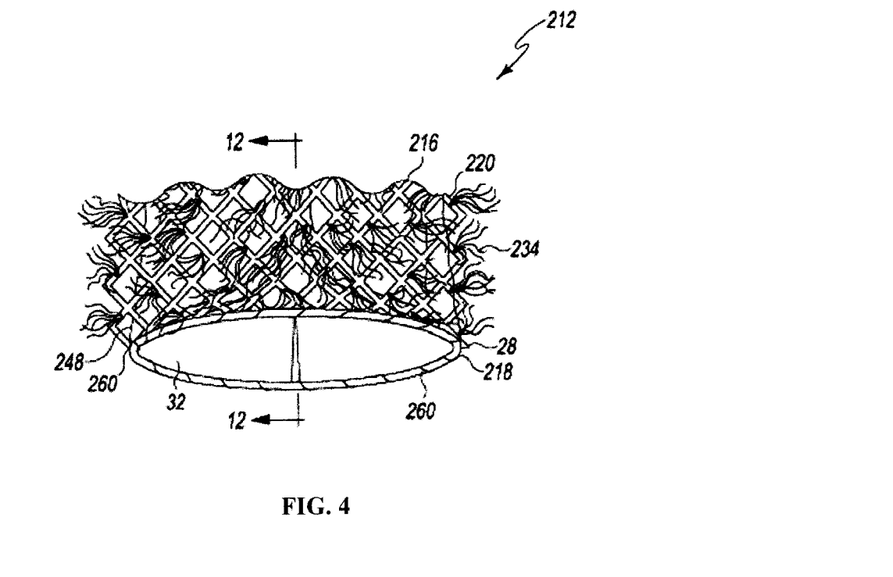
FIG. 4 illustrates an enlarged, partial, perspective view of the TVR of FIG. 1 according to one or more embodiments disclosed herein.
Figure 5:
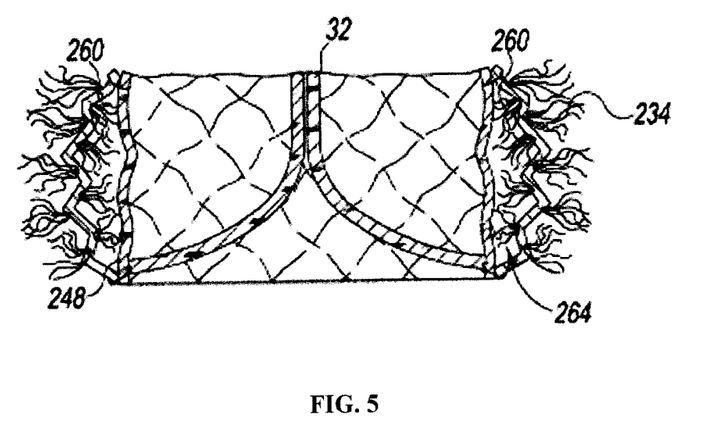
FIG. 5 illustrates a side, cross-section view of the TVR of FIG. 1 according to one or more embodiments disclosed herein.
Figure 6:
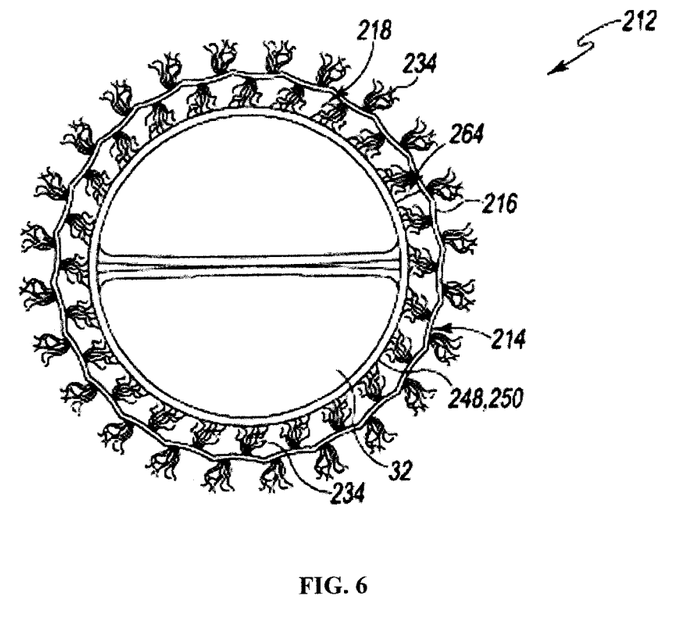
FIG. 6 illustrates a top facing, cross-section view of the TVR of FIG. 1 according to one or more embodiments disclosed herein.

Referring now to FIG. 4, the inner frame 218 of the dual-frame component 214 is secured to the outer frame 216 via a plurality of stitches 260. It should be appreciated that in other embodiments soldering, welding or other fasteners may be used to secure the inner frame 218 to the outer frame 216. As shown in FIGS. 4-7, the inner frame 218 and the valve component 32 are positioned in the passageway 232 defined in the self-expanding frame 216. When the inner frame 218 is unexpanded, the outer surface 248 of the stent 244 is spaced apart from the fibers 234 attached to the outer frame 216. In the illustrative embodiment, a gap 264 is defined therebetween, and the gap 264 has a magnitude of about 2 mm to about 3 mm.

Figure 7:
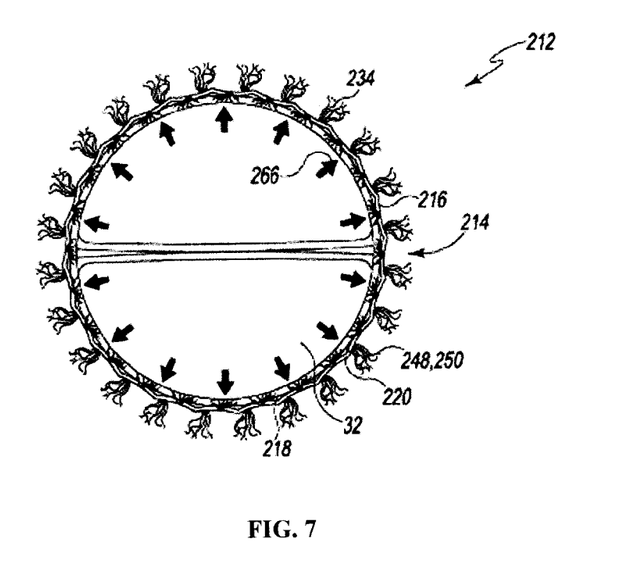
FIG. 7 illustrates the TVR of FIG. 6 where the inner frame has been expanded (out of the patient) to compress with the outer frame according to one or more embodiments disclosed herein.

As shown in FIG. 7, the balloon-expandable inner frame 218 may be expanded in the direction indicated by arrows 266. As described above, the diameter 230 of the proximal section 220 of the outer frame 216 is oversized relative to the diameter of the aortic annulus 210. As such, when the component 212 is implanted, the proximal section 220 is reduced to the diameter of the annulus 210. Because the expanded diameter 252 of the stent 244 is greater than the diameter of the annulus, the outer surface 248 of the stent 244 engages the fibers 234 (and hence the inner surface of the proximal section 220 of the outer frame 216) through the covering material 250. In that way, the gap 264 is closed, and the fibers 234 and the covering material 250 create a seal between the inner frame 218 and the outer frame 216.

To implant an endograft device 10 that includes proximal component 212 in the patient's aorta 16, a surgeon may obtain open exposure or percutaneous access to the common femoral artery.

Figure 8:
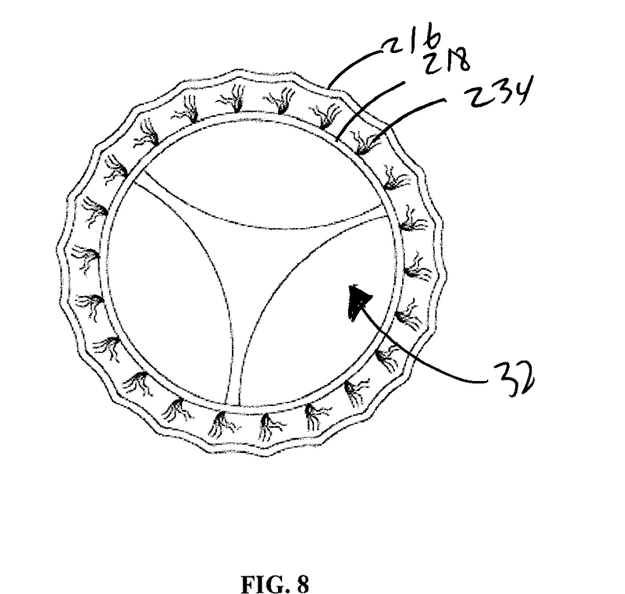
FIG. 8 illustrates a top facing, cross-section view of a TVR according to one or more embodiments disclosed herein.

An improved valve assembly is illustrated in FIG. 8. The valve is shown with the inner frame spaced-apart from the outer frame, which can be employed in certain embodiments. However, the spacing is shown here for clarity purposes. In practice, the inner frame, which may be a polymer or other graft type frame as disclosed herein, houses the valve. An outer stent frame may be a gridded or open cell stent frame that is stitchably or otherwise engaged with the inner frame. There may or may not be a gap between the inner frame and outer frame before deployment. A distal portion of the valve leaflets may be coupled to the outer frame via commissures.

With continued reference to FIG. 8, the valve assembly includes a plurality of fibers that extend from the inner frame and through the gridded openings in the outer metallic frame. In this manner, a low profile for the valve assembly as a whole is created, and the fibers press against the aortic annulus once deployed. The fibers may be radially extending strands as illustrated. The fibers may be stitchably or adhesively engaged with the inner graft frame, or they may be engaged with a pile surface that is then engaged with the inner graft frame. The fibers may extend through a series of rows of the gridded outer frame, or may form a concentric band, or may extend further longitudinally than illustrated in FIG. 10.

Due to the fact that the native valve leaflets are left in place, the aortic annulus will define a slightly arcuate triangular shape.

This slightly arcuate triangular shape creates the need for the sealing to prevent paravalvular leaks. In this manner, the fibers provided in the inventions disclosed herein seal against the annulus and can even seal if the annulus changes shape with time.

A further embodiment is illustrated in FIG. 10. In this embodiment, aspects of the invention shown in FIGS. 8 and 9 are combined with a graft covering concept. There is thus provided a valve assembly that includes an outer graft covering, combined with fibers extending from the inner stent frame. The fibers are shown occupying one row of the gridded outer frame, however, the fibers may occupy more or less. The fibers can even be present in the rows of the gridded outer frame that are covered by the graft material, and press against the graft material creating a further seal between the graft material and fibers. This embodiment thus provides a graft covering for sealing proximally (below) the native valve leaflets of the patient, and the fibers for sealing against the native valve leaflets of the patient in circumstances where the device is deployed/positioned in such an arrangement.

Figure 11:
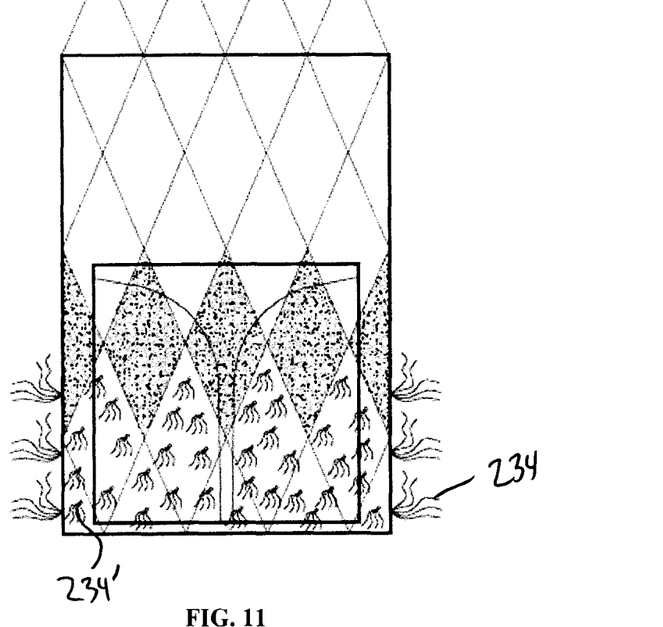
FIG. 11 illustrates a side, cross-section view of a TVR according to one or more embodiments disclosed herein.
Figure 12:
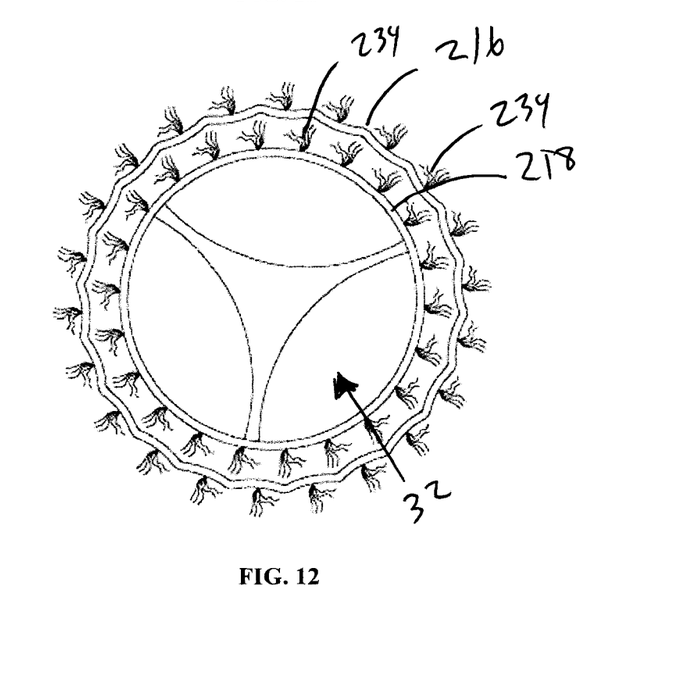
FIG. 12 illustrates a top, cross-section view of a TVR according to one or more embodiments disclosed herein.

An alternate embodiment in which the fibers are located proximally relative to the graft is illustrated in FIG. 10. In another embodiment illustrated in FIG. 11, the fibers can emanate from the inner frame within one row of the metal frame, and emanate from the outer frame within another row of the metal frame.

Each of the inner frame and outer frame may be self-expanding and/or balloon expandable. In one or more embodiments, the outer frame may be self-expanding and the inner frame balloon expandable, thus pressing the fibers into contact with the annulus of the patient.

A further embodiment is illustrated in FIG. 15, which is similar to FIG. 8 embodiment but additionally includes further fibers on an outside of the valve frame.

The additional fibers may be individually stitched to the outer frame, or they may be part of a pile-type construction where the fibers extend out of a backing, and the backing is engaged with the outer stent frame.

Another embodiment is illustrated in FIG. 16 in which the inner stent frame has sections "scored" out where the fibers are not present. In this manner, when the inner stent frame is pressed against the outer stent frame, the fibers fit into the gridded structure but do not get pressed between the inner stent frame and outer stent frame. The portion shown in 16 may be a pile-type construction that is configured for being stitched or otherwise engaged with the inner frame, or the inner frame may be constructed in this manner.

Any of the embodiments may include a distal section like is shown in the prior art device described herein, namely feature 64, with the distal section either being uncovered or covered, and providing a second contact point with the annulus of the patient.

Figure 13:
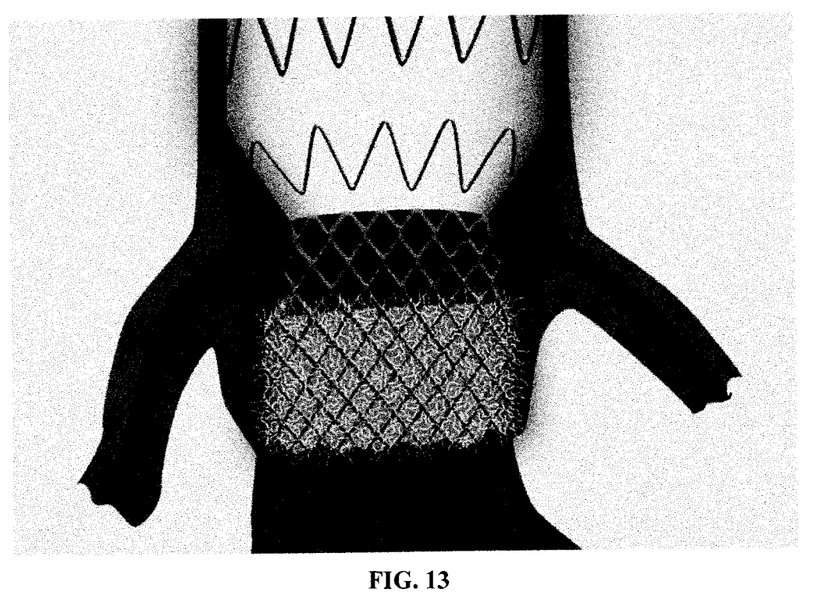
FIG. 13 illustrates a deployed view of a TVR within the aorta according to one or more embodiments disclosed herein.

An illustration of one of the embodiments deployed within the aorta is shown in FIG. 13. Here the outer seal is shown in engagement with native valve leaflets of the patient.

We claim:

1. A heart valve assembly comprising:
   a frame formed from a metallic material and that defines a gridded configuration;
   a covering extending around a prosthetic heart valve for providing sealing to the heart valve,
   wherein the covering is one of polyester, PTFE, ePTFE, or a polymer;
   wherein the frame is secured to the covering by a plurality of stitches,
   a first plurality of radially extending fibers that extend outwardly of the frame and are in contact with the frame;
   a second plurality of radially extending fibers that extend from the covering and through the frame to form a seal positioned outwardly of the frame.

* * * * *